United States Patent [19]

Albert

[11] 4,172,714
[45] Oct. 30, 1979

[54] DRY COMPACTIBLE, SWELLABLE HERBICIDAL COMPOSITIONS AND PELLETS PRODUCED THEREFROM

[75] Inventor: Robert E. Albert, Wilmington, Del.

[73] Assignee: E. I. Du Pont de Nemours and Company, Wilmington, Del.

[21] Appl. No.: 887,343

[22] Filed: Mar. 20, 1978

Related U.S. Application Data

[63] Continuation-in-part of Ser. No. 808,664, Jun. 21, 1977, abandoned.

[30] Foreign Application Priority Data

Dec. 20, 1977 [CO] Colombia .............................. 170955

[51] Int. Cl.$^2$ .............................................. A01N 9/22
[52] U.S. Cl. .......................................... 71/93; 71/90; 71/92; 71/106; 71/120; 71/DIG. 1
[58] Field of Search ............... 71/DIG. 1, 92, 93, 120, 71/90

[56] References Cited

U.S. PATENT DOCUMENTS

| | | | |
|---|---|---|---|
| 2,992,090 | 7/1961 | Littler | 71/93 |
| 3,832,468 | 8/1974 | Hyson et al. | 424/300 X |
| 3,914,230 | 10/1975 | Hyson | 71/92 X |
| 4,055,974 | 11/1977 | Jackson, Jr. | 71/DIG. 1 |
| 4,058,124 | 11/1977 | Yen | 71/DIG. 1 |

OTHER PUBLICATIONS

Iler, "The Colloidal Chemistry of Silica", pp. 190–197, Cornell Univ. Press; Ithica, N.Y., (1955).

*Primary Examiner*—Joseph Paul Brust

[57] ABSTRACT

A dry compactible, herbicidal composition consisting essentially of an active herbicidal compound, a swelling bentonite, a normally liquid polyethylene glycol, anhydrous sodium sulfate, urea, an inert diluent and water can be dry compacted into an herbicidal pellet which is resistant to impact and crushing and which swells and disintegrates when contacted with small amounts of liquid water to release the herbicidal compound.

5 Claims, No Drawings

DRY COMPACTIBLE, SWELLABLE HERBICIDAL COMPOSITIONS AND PELLETS PRODUCED THEREFROM

CROSS REFERENCE TO RELATED APPLICATIONS

This application is a continuation-in-part of application Ser. No. 808,664, filed June 21, 1977 (now abandoned).

BACKGROUND OF THE INVENTION

This invention relates to herbicidal compositions for controlling undesirable brush in rangelands and woodlands and, more particularly, to herbicidal compositions which are dry-compacted into swellable pellets having improved properties for aerial application and use in low-rainfall areas.

Undesirable weeds and thorny brush growth such as mesquite, huisache, yaupon, McCartney rose and the like infest millions of acres of rangeland. Once heavily infested, such rangelands are no longer suited for livestock grazing.

Broad-spectrum herbicides, which are normally applied to infested acreage with aerial or ground sprays, or by a dry granule broadcast method, destroy not only the undesirable brush, but also much needed grasses and other ground cover. Although selective herbicides can be used to avoid injury to ground cover, the high concentrations of active ingredient which are needed to destroy the hardy brush varieties can make the cost of selective herbicides prohibitive.

In woodlands, particularly pine woodlands which are "farmed" to produce trees for the pulp and paper industry, brush growth can retard the development of young trees and may increase the planting-to-harvesting cycle by as much as eight years. Broadcast applications of conventional herbicide formulations at rates high enough to control the undesirable brush can kill or severely damage the young trees.

The compositions of this invention are aimed typically at woodland and brush areas which are arid and have low rainfall. Any herbicide which is to be useful for this type of area must require very little water to make the material active in the soil. Furthermore, economy of application, where large areas and difficult terrain are involved, favors the use of airplanes.

With certain herbicides—such as the ones used in the compositions of this invention—selection between the large brush that must be controlled vs. the seedling trees or grass for grazing whose growth the treatment should promote, can be obtained by applying the herbicide as large pellets or briquettes on a grid pattern, for example on a 1-3 meter grid. As the herbicide is moving downward from the relatively few loci of the grid, the large root systems of the brush can pick up a lethal dose of herbicide while in the remaining areas the grass or the seedling trees grow without damage.

This combination of application requirements can only be met with large pellets or balls which have very special physical properties. The handling, shipment, storage and use of such material requires that these pellets be hard, crush and impact resistant, and unaffected by high relative humidity, while, at the same time, after application, the pellets must swell and disintegrate after only small amounts of rainfall to release the active herbicide.

Thus, there is need for a composition having a critical set of properties which are in part contradictory and are difficult to attain. Furthermore, it is important to produce these compositions, i.e. these pellets and balls, economically. Hence, expensive wet extrusion and drying processes should be avoided in favor of dry-compaction or briquetting.

SUMMARY OF THE INVENTION

The present invention provides a dry-compactible composition consisting essentially of about 5 to 25% by weight of a herbicide selected from the group consisting of 5-bromo-3-sec-butyl-6-methyluracil (hereinafter bromacil), [3-(3,4-dichlorophenyl)-1,1-dimethylurea] (hereinafter diuron), bromacil-diuron complex, 3-cyclohexyl-6-(dimethylamino)-1-methyl-s-triazine-2,4(1H,3H)-dione (hereinafter Velpar® weed killer), karbutilate, tebuthiuron and N-[(4,6-dimethoxy-1,3,5-triazin-2-yl)aminocarbonyl] benzenesulfonamid and mixtures thereof, 20 to 60% by weight of swelling bentonite, 5 to 15% by weight of anhydrous sodium sulfate, 10 to 25% by weight of urea, 2 to 10% by weight of a polyethylene glycol with a weight-average molecular weight ranging from 200 to 600, 0–5% of a die release agent selected from the group consisting of stearic acid, calcium stearate or magnesium stearate, 1 to 12% by weight and 0 to 30% of an inert diluent.

The term "bromacil-diuron complex" as used herein means the 1:1 molar complex of the two components as describeed in U.S. Pat. No. 3,914,230, the teachings of which are incorporated herein by reference.

Pellets prepared by dry compacting these compositions are particularly useful for aerial application to woodlands and rangelands for controlling undesirable brush. The pellets of this invention combine the advantages that they can be produced by dry compaction (e.g., the composition does not require a wet extrusion step followed by heating and/or drying), are impact- and crush-resistant while dry, and are highly resistant to disintegration in high-humidity atmospheres. Once applied, these pellets will swell and disintegrate rapidly and hence will release the active herbicide when exposed to only a small amount of liquid water and will not re-harden when dried.

DETAILED DESCRIPTION OF THE INVENTION

Improved physical properties can be achieved in herbicide compositions used for controlling brush on rangelands and woodland by dry-compacting a composition consisting essentially of about 5 to 25% by weight of active ingredient, about 20 to 60% by weight of a swelling bentonite, about 5 to 15% by weight of anhydrous sodium sulfate, about 10 to 25% by weight of urea, about 2 to 10% by weight of a polyethylene glycol with a weight-average molecular weight ranging from 200 to 600, about 0 to 5% by weight of a die release agent, about 1 to 12% by weight of water and from 0 to 30% by weight of an inert diluent into pellets or balls having a density in the range of about 0.5 to 1.75 grams/milliliter and a volume in the range of about 0.75 to 2.0 cubic centimeters. The term "pellet" is used herein to mean a shaped body such as a briquette, bolus, ball or any other suitable shape.

The phase "consisting essentially of" is not intended to limit the claims so as to exclude other ingredients when the specification clearly indicates other constituents may be present. The phrase does exclude ingredients which would affect the basic and novel characteristics of the invention defined by the claims.

The pellets of this composition have a critical balance of physical properties which is important in the control of undesirable brush in arid regions used for grazing or forestation. The process and composition combine to yield a pellet which is hard, crush- and impact- resistant, and unaffected by high relative humidity in storage. Yet, after application, the pellet can swell and disintegrate upon contact with only a small amount of liquid water (rainfall) to activate and release the herbicidal active ingredient.

Generally, the pellets of this invention are applied by aerial means in a low-density pattern over the acreage to be treated. Spacing the pellets on the average about 1 to 3 meters apart provides for optimum distribution of active ingredient. Other grid patterns and pellet spacing may also be used.

The compositions of this invention will typically contain the following essential ingredients: (1) an active ingredient having the desired biological activity; (2) a swelling bentonite to accomplish structural disintegration of the pellet on contact with liquid water; (3) anhydrous sodium sulfate to prevent the pellet from rebonding if drying should occur after the pellet has been initially exposed to liquid water; (4) an inert diluent to adjust the weight and composition of the pellet and a combination of (5) urea; (6) polyethylene glycol having a weight-average molecular weight of 200–600; and (7) water below about 12% by weight of the total composition to serve as plasticizer, binder and lubricant during dry pressing.

As used herein the term "swelling bentonite" means absorptive clays generally described as montmorillonites and capable of expanding their lattice structure upon the absorption of water. Such clays are described by R. K. Iler; The Colloidal Chemistry of Silica and Silicates, pp. 191–198, Cornell University Press, Ithica, N.Y., 1955. Examples of commercially available swelling bentonites are: Volclay ®, Wy-O-Gel ®, and other Wyoming bntonites.

The active compounds useful in this invention are herbicides selected from the group consisting of bromacil, diuron, bromacil-diuron complex, mixtures of bromacil-diuron complex with bromacil or diuron, Velpar ® weed killer, karbutilate, tebuthiuron, and N-[4,6-dimethoxy-1,3,5 triazine 2-yl)-aminocarbonyl]benzene sulfonamide, and combinations of these.

The ingredients are dry blended in any suitable blending apparatus in the desired proportions. The blended ingredients may also be ground in a hammer-mill, ball mill, rod mill or other suitable grinding equipment. The composition is reblended after milling to insure uniformity. Dry compacting is accomplished by conventional methods to form the water swellable pellets. Briquetting and pill pressing are particularly suitable methods for dry compacting these compositions. In the case of some mixtures of ingredients (depending upon the properties of the active herbicidal chemical, the particle size range and the proportions of the ingredients) deaerating the ground and blended composition may be necessary prior to the dry compacting operation in order to prepare a pellet with the required crushing strength and impact resistance. Deaerating can be accomplished economically by precompacting the composition by passing the mixture through: (1) "squeeze" rolls; or (2) a deaerating (compacting) screw feeder immediately prior to dry compacting. The bulk density of deaerated mixtures can be increased up to two to three times that of the aerated mixture. The deaerated mixtures can be compacted by roll briquetting at much higher rates than the corresponding aerated mixtures. In order to prevent sticking of the compacted material in the dry-forming die a small amount of a die release agent may be added to the composition. Suitable die release agents are stearic acid, calcium stearate or magnesium stearate. The die release agent is blended into and ground with the other ingredients.

Dry processing prevents premature swelling of the bentonite and obviates the need for any drying step in preparing the pellets. It should be noted that bentonites swell when initially exposed to small amounts of liquid water for about 5 to 120 minutes. If dried under mild conditions such as might exist in rangelands, only excess water is removed by evaporation. The water that produces the swelling by absorption into the lattice of the bentonite is not evaporated. Therefore, swelling generally occurs only once. However, wet bentonite will dry in time and become hard, resulting in a reduced surface area from which the active ingredient may only be slowly leached by successive wetting. To prevent the bentonite from hardening, anhydrous sodium sulfate is incorporated into the composition. Anhydrous sodium sulfate is used because it is capable of forming stable hydrates from 0.5 moles of water up to 10 moles of water per mole of anhydrous salt.

The binder material for the composition of this invention includes urea because of its water solubility and biological considerations. The presence of small amounts of water in the composition, preferably from about 1 to 12% by weight, more preferably from about 4–8% by weight, acts as a plasticizer for the urea and aids the bonding process during dry compaction. Water-insoluble and slowly soluble binders, such as sodium silicate, retain their binding properties for extended periods in the presence of liquid water and would inhibit the swelling of the bentonite. Other water soluble binders such as sugar, polyvinyl alcohol, and polyvinyl pyrollidone generally require more than 12% by weight of water for effective binding. Their rates of solubility are also much less than urea so that they do not cooperate as efficiently with the other ingredients of the compacted composition to allow for swelling and as rapid a release of the active ingredient.

The polyethylene glycol operates within the composition as a liquid reservoir together with the water. Polyethylene glycol also protects against water migration among the ingredients of the composition which could result from temperature changes during storage. Thus, premature swelling and crumbling of the pellets is prevented. The pellets of this invention may be stored in sealed containers for up to about two years without any significant or deleterious change in chemical or physical properties.

The polyethylene glycol should have from about 200 to 600 weight average molecular weight. Lower molecular weight glycols, for example ethylene glycol and diethylene glycol, exhibit relatively high vapor pressures and tend to volatilize at high ambient temperatures. High molecular weight glycols, normally liquid at ambient temperatures, are generally viscous and difficult to distribute uniformly during preparation of the composition.

Inert diluents may be incorporated into the composition up to about 30% by weight of the dry compacted product to adjust the weight of the pellet. Preferred diluents include, but are not limited to, inert clays such as non-swelling bentonites, sub-bentonites (Panther Creek clay), attapulgites (Attaclay ®), kaolinites (Barden clay) and diatomaceous earth.

Ground or aerial application techniques can be used to distribute the pellets of this invention in the desired pattern over the area to be treated. Where large or remote surface areas are to be treated, aerial application is the most economical and preferred method. The pellets are released from an aircraft at a rate which will achieve the desired grid spacing and, hence, distribution of active ingredient, when the pellets come to rest on the ground.

By the term grid spacing or grid pattern is meant an average spacing of pellets over a hectare of treated area. For example, to apply 1.12 kg of active ingredient in a grid pattern of one hectare using pellets containing 15% by weight of active herbicidal chemical requires 2990 pellets (7.5 kg) applied in a square grid pattern with an average spacing between adjacent pellets of 1.8 meters. Precise spacing cannot be absolutely maintained between each pair of pellets due to effects of external forces such as air turbulence, contact with canopy foliage, deflection by branches and rebounding or bouncing of some pellets which occasionally strike exposed hard ground or other firm objects on the ground surface. However, these slight disturbances in the precise grid pattern desired do not affect the overall biological performance of the pellets under field conditions.

At the ground location of each pellet any destruction of ground cover by released herbicide is generally confined to a circular area no larger than about 30 centimeters in diameter. The area of the denuded spots is determined by the soil conditions controlling the ground penetration rate of the active ingredient which is being released from the pellet, the amount and rate of rainfall, and the particular active ingredient and its release rate from the pellet.

A grid distribution of the pellets creates generally conical "columns" of herbicide within the soil with the apex at the surface location of the pellets. When released from the pellet by small amounts of liquid water, such as from dew or rain, the active ingredient penetrates downwardly through the soil. This type of distribution and penetration allows the active ingredient to reach the roots of hardy brush species and avoid contact with the shallow rooted, more desirable grasses and ground cover. Only a small portion of a plant or tree root system need be exposed to the herbicide to retard or eliminate it.

The swelling and crumbling of the pellets of this invention when contacted with small amounts of liquid water not only permits the active ingredient to be released quickly from the formulation, but also destroys the physical structure of the pellet. Thus, small animals such as rabbits and mice are much less likely to find a pellet intact and be exposed to the active ingredient. The active herbicide is quickly released to the soil from the pellet when swelling occurs, and small animal population is protected.

Usual application techniques employ either mechanical "slingers" or pneumatic devices which distribute the pellets over swaths or bands up to about 15 meters wide. The term "slinger" is used to define a rapidly rotating disk having radial spaced baffles. The pellets are dropped onto the "slinger" at a controlled rate, are struck by the baffles and impelled a given distance from the "slinger" to achieve the desired swath width.

Of the pneumatic applicators, one is a "fish tail" type used for aerial seeding and fertilizer applications from fixed wing aircraft. The herbicide pellets are dropped into a ram air section having an air stream velocity of about 40 to 55 meters/second and forced by the air stream against baffles in the "fish tail" discharging area. A second type of pneumatic applicator is adapted for use with helicopters. It employs a blower to provide a high velocity air stream which ejects the pellets in a swath pattern from a duct system into which the pellets are fed.

It will be appreciated by those familiar with application techniques that the pellets are subject to a multiplicity of forces during application. As the pellets fall to the ground they strike the leaf canopies and branches of taller trees and brush. They are also affected by the nature and velocity of any crosswinds as they fall.

The pellets of this invention provide the desired combination of physical properties and exhibit high crushing and impact strength to resist damage from shipping, handling and the forces associated with application. Because of their improved physical properties, the pellets of this invention can be better controlled during aerial application to achieve the desired grid pattern. The pellets are dense enough to resist deflection by crosswinds and the leaves of brush and tree canopies.

Crushing strength is determined by first dry-compacting the desired formulation, after blending and grinding, to obtain a cylindrical sample pellet 16 mm in diameter by about 9 to 11 mm long. Compacting is accomplished by applying 1400–1450 kg/cm$^2$ pressure to a piston which compacts the loose formulation in a cylindrical die. After compaction, the pellet is placed horizontally between two horizontal parallel steel plates and the plates are loaded until crushing occurs. Pellets of this invention resist crushing with loads less than about 7500 grams or 3.7 kg/cm$^2$.

Impact resistance is measured by dropping a sample pellet as compacted above onto a smooth, hard horizontal surface such as concrete or steel from a height of 3 meters. Pellets of this invention normally resist breakage for 5 drops.

The reaction of a sample pellet to wetting with liquid water and subsequent drying is determined by placing the pellet into a covered Petri dish and applying 0.5 ml (5 drops) of water thereto. Swelling and crumbling is observed during the first 2 to 5 hours. The pellets of this invention will crack immediately after wetting and swell to about 2 to 3 times their original volume during the observation period. The cover is then removed and the pellets are allowed to dry at about 23° C. and between about 25 to 60% R.H. When dried the pellets of this invention do not rebond but remain crumbled.

Apparent density of the pellets is measured by mercury displacement. The density of the pellets of this invention is such that mercury will not penetrate the pores thereof. Pellets of this invention exhibit an apparent density of about 1 g/ml or greater.

Composition ranges of the pellets of this invention are given in Table 1:

TABLE 1

| Ingredient | Composition % by Weight |
| --- | --- |
| Active Herbicidal Chemical | 5–25 |
| Swelling Bentonite | 20–60 |
| Anhydrous Sodium Sulfate | 5–15 |
| Urea | 10–25 |
| Polyethylene Glycol | |

TABLE 1-continued

| Ingredient | Composition % by Weight |
| --- | --- |
| (200–600 Wt. Average Mol. Wt.) | 2–10 |
| Total Water | 1–12 |
| Die Release Agent | 0–5 |
| Inert Diluent | 0–30 |

More preferred composition ranges are shown in Table 2:

TABLE 2

| Ingredient | Composition Range, % by Weight |
| --- | --- |
| Active Herbicidal Chemical | 8–15 |
| Swelling Bentonite | 30–50 |
| Anhydrous Sodium Sulfate | 5–15 |
| Urea | 10–20 |
| Polyethylene Glycol (200–600 Wt. Average Mol. Wt.) | 2–10 |
| Total Water | 4–8 |
| Die Release Agent | 0–5 |
| Inert Diluent | 10–25 |

Optionally, small quantities of dispersant and/or wetting agent can be included in the composition.

Particular compositionss for grid applications are selected on the basis of the following considerations: (1) amount of active herbicidal chemical to be applied per unit area: (2) grid spacing; and (3) total weight of composition to be applied per unit area. The weight of the pellets is generally determined by the metering accuracy of the aerial application equipment. Usually about 10–12 kg/hectare is the minimum weight of total composition which can accurately be applied to a given area. In some instances, however, total weight can be as low as 6 kg/hectare where well constructed, accurately calibrated equipment is used. For example, to apply 1.12 kg active chemical per hectare in a total of 11.2 kg of composition in a generally square grid pattern of 1.8 m × 1.8 m average spacing requires that the composition contain about 10% by weight of the active chemical and be uniformly distributed as 2990 compacted pellets per hectare. Each pellet will contain about 0.375 g of herbicidal chemical. Other compositions and grid spacings are given in Table 3.

TABLE 3

Compositions and Rates for Grid Application

| Average Square Grid Spacing Meters | Pellets/ Hectare | Pellet Composition Wt. % Active Ing. | Application Rate, Kg/hectare | | w/Pellet, g | |
| --- | --- | --- | --- | --- | --- | --- |
| | | | Active | Total | Active | Total |
| 1.8 × 1.8 | 2990 | 15 | 1.12 | 7.5 | 0.375 | 2.50 |
| 1.2 × 1.2 | 4480 | 15 | 2.24 | 14.9 | 0.500 | 3.33 |
| 1.2 × 1.2 | 4480 | 20 | 2.24 | 11.2 | 0.500 | 2.50 |
| 1.8 × 1.8 | 2990 | 20 | 4.48 | 22.4 | 1.50 | 7.50 |
| 1.8 × 1.8 | 2990 | 25 | 6.72 | 26.9 | 2.25 | 9.00 |

This invention is further described by the following examples. Velpar ® 90 Weed Killer is a composition which contains about 89–91% by weight of 3-cyclohexyl-6-dimethylamino)-1-methyl-s-triazine-2,4-(1H, 3H)dione and about 11–9% by weight of inert diluents and process impurities.

EXAMPLE 1

The following ingredients are blended together:

| Ingredient | Wt. (kg) |
| --- | --- |
| Velpar ® 90 Weed Killer | 5.59 |
| Anhydrous Sodium Sulfate | 4.65 |
| Prilled Urea | 7.30 |
| Volclay 90 Swelling Bentonite (6.7% water) | 20.64 |
| Attaclay Inert Diluent (3.7% water) | 8.51 |
| Polyethylene Glycol 200 | 2.50 |
| Water | 0.80 |

After thorough blending the composition is ground in a bantam hammer mill (Mikropul Corp., Summit, N.J.) using a screen having 1 mm dia. holes. The particle size range of the ground formulation indicated 5.9 wt. % larger than 150μ, 30.2 wt. % larger than 74μ and 47.6 wt % smaller than 44μ.

The ground composition is dry compacted using a model 50 KHD briquetting press (Klockner-Humboldt-Deutz Ag., Köln, West Germany) with rolls having 1. cc pockets to form briquettes of 1. cc volume weighing about 2.1 g each. The briquettes are physically stable when exposed to 95% RH atmosphere for 100 hours and exhibit a crushing load of 11,000 g. The pellets swell and crumble after being contacted with 1 ml of liquid water.

EXAMPLE 2

This example demonstrates the effect of removing the polyethylene glycol from the composition.

The composition of Example 1, without the polyethylene glycol 200, is prepared by blending and grinding. In this instance, however, cylindrical shapes, 1.27 cm in diameter are formed by pressing the composition in a cylinder and ram die using a laboratory press and a pressure of about 450 kg/cm² gauge.

The cylindrical shapes are exposed to 85% and 100% RH atmospheres for 16 hours. The shapes exposed to 85% RH swell about 10% volumetrically, exhibit surface tackiness and are cracked. Those exposed to 100% RH swell about 25% volumetrically, exhibit surface tackiness and are so severely cracked they cannot be handled without crumbling.

EXAMPLE 3

This example demonstrates the effect of removing the sodium sulfate from the composition.

11.4 g of Velpar ® 90 weed killer, 44.4 g of the Volclay 90, 33.3 g of Attaclay and 11.2 g of crystal urea are thoroughly blended and ground as in Example 1. The ground composition is pressed as in Example 2 to form dense, strong cylindrical shapes.

The shapes are contacted with about 0.2 ml of liquid water which is equivalent to about 0.5 cm of rain. The compacted shapes swell and crack initially. When allowed to dry at 23° C. and 40% RH the cylinders rebond into strong, coherent structures. Rewetting does not cause swelling and recracking.

EXAMPLE 4

The following ingredients are blended together:

| Ingredient | WT., Kg | WT. % |
|---|---|---|
| Velpar ® 90 Weed Killer | 5.59 | 11.18 |
| Anhydrous Sodium Sulfate | 4.65 | 9.30 |
| Prilled Urea | 7.30 | 14.60 |
| Volclay 90 (6.7% water) Bentonite | 20.64 | 41.28 |
| Attaclay (3.7% water) Diluent | 7.52 | 15.04 |
| Polyethylene Glycol 200 | 2.50 | 5.00 |
| Stearic Acid, Die Release Agent | 1.00 | 2.00 |
| Water | 0.80 | 1.60 |
| | 50.00 | 100.00 |

After thorough blending the mixture is ground in a hammer-mill (No. 1 Mikro-polverizer, Mikropul Corp., Summit, N.J.) using a screen with 1 mm dia. holes.

The ground composition is dry-compacted using a Model 220 Komarek Roll Briquetter (K. R. Komarek Inc., Elk Grove Village, Ill.) using rolls having 2.2 cc volume to form 2.2 cc bolus shaped briquettes weighing 3.75 g each and containing 10 wt % of active herbicide.

The briquettes are physically stable to 100 hrs. exposure at 90% RH, exhibit a crushing load >11.0 kg and exhibit an impact resistance >10 drops. When wetted with 1 ml of water per briquette, the briquettes swell and crumble and do not rebond upon drying.

EXAMPLE 5

The briquettes of Example 4 were hand distributed on a 1.8 meter×1.8 meter (6 ft.×6 ft.) square grid pattern over four separate 0.1 hectare (0.25 acre) plots at an over application rate of 11.2 kg/ha (10 lb/acre) of briquettes and providing 1.12 kg/ha (1 lb/a) of active herbicide. The plots contained seedling loblolly and short-leaf pines, the desired species being "farmed" to provide a source of pulpwood. The plots also contained the undesirable hardwoods: dogwood; hickory; hornbean; maple; oaks; sweetgum; and sourwood, which compete with the pines for food, water and sunlight and seriously retard their growth.

Five months after the treatments the undesired species were defoliated and dying with no apparent injury to the pine species. One year after the treatments the hardwood species were eliminated. The pine seedings in the treated plots exhibited larger growth and vigor compared to similar adjacent but untreated plots.

EXAMPLE 6

The briquettes of Example 4 were applied from a helicopter using a Simplex ® Pneumatic Seed applicator to distribute 22.4 kg/ha (20 lb/A) of briquettes, in a square grid pattern, 1.3 meters×1.3 meters (4.25 feet×4.25 feet) on 1 ha (2.47 A) loblolly) and short-leaf pine seedling plots. The seedling plots were infested with dogwood, blackjack oak, redoak, postoak, sourwood, hickory, sweetgum and yellow poplar.

Five months after treatment the undesired hardwood were completely eliminated with no damage to either loblolly or short leaf pine. The pine species showed much greater growth and vigor as compared to adjacent untreated plots.

EXAMPLE 7

The following ingredients are blended together and ground in a laboratory hammer-mill:

| | MIXTURE A | |
|---|---|---|
| Ingredient | WT. (g) | W % |
| Anhydrous Sodium Sulfate | 18.6 | 10.5 |
| Carbowax ® 200 | 10.0 | 5.6 |
| Volcaly ® 200 | 77.0 | 43.4 |
| Crystal Urea | 29.2 | 16.4 |
| Attaclay ® | 32.8 | 18.5 |
| Water | 10.0 | 5.6 |
| | 177.6 | 100.0 |

10 g portions of Mixture "A" were blended with 2.3 g of each of several wettable powder herbicides to prepare 12.3 g of each of the following compositions:

| Sample | Mixture "A" (g) | Active Ingredient Compound | WT. % | Final Composition WT. % Active Herbicide |
|---|---|---|---|---|
| 1 | 10 | Diuron | 80 | 15 |
| 2 | 10 | Bromacil | 80 | 15 |
| 3 | 10 | Bromcil/Diuron | 80 | 15 |
| 4 | 10 | Tebuthiuron | 80 | 15 |
| 5 | 10 | Karbutilate | 80 | 15 |

3.75 g portions of each of the five compositions are dry compacted into cylindrical pellets as in Example 2. The pellets exhibit the following properties.

| Sample | Impact Strength Drops | Crushing Load kg | Humidity Stability 24 Hrs., 88% RH, WT gain, % | Swelling 1.0 mm(water) |
|---|---|---|---|---|
| 1 | 8 | 9.0 | 5.0 | Crumbled |
| 2 | >10 | 10.0 | 4.0 | Crumbled |
| 3 | 9 | 9.5 | 4.0 | Crumbled |
| 4 | >10 | 11.5 | 4.5 | Crumbled |
| 5 | >10 | 11.0 | 4.5 | Crumbled |
| Briquette of Example 1 | >10 | 11.0 | 3.5 | Crumbled |

EXAMPLE 8

The following compositions are thoroughly blended and ground using a laboratory hammer-mill:

| Sample | 1 | 2 | 3 | 4 |
|---|---|---|---|---|
| Ingredients, WT % | | | | |
| Velpar ® 90 Weed Killer | 11.2 | 11.2 | 11.2 | 11.2 |
| Volclay ® 200 | 20.0 | 40.0 | 60.0 | 70.0 |
| Ahyd. Sodium Sulfate | 10.0 | 10.0 | 8.0 | 5.0 |
| Urea | 15.0 | 15.0 | 8.0 | 10.0 |
| Carbowax ® 200 | 5.0 | 5.0 | 5.0 | 3.8 |
| Attaclay ® | 32.8 | 13.8 | 5.8 | 0.0 |
| Stearic Acid | 1.0 | 1.0 | 1.0 | 0.0 |
| Water | 5.0 | 4.0 | 2.0 | 0.0 |
| Total | 100.0 | 100.0 | 100.0 | 100.0 |

The ground compositions are dry compacted as in Example 7, and the pellets exhibit the following properties.

| Sample | Impact Strength No. of (Drops) | Crushing Load (kg) | Swelling (1.0 ml water) |
|---|---|---|---|
| 1 | >10 | 6.0 | Swells & Cracks |
| 2 | >10 | 11.5 | Crumbles |
| 3 | 5 | 10.5 | Crumbles |
| 4 | 0 | 8.5 | Crumbles |

Sample 4 contains insufficient binder to form a strong impact and crush resistant pellet.

What is claimed is:

1. A herbicidal composition suitable for dry-compacting into crush and impact resistant, water swellable pellets, consisting essentially of about 5–25% by weight of a herbicide selected from the group consisting of bromacil, diuron, bromacil-diuron complex, 3-cyclohexyl-6-(dimethylamino)-1-methyl-s-triazine-2,H(1H,3H)-dione, karbutilate, tebuthiuron, N-[(4,6-dimethoxy-1,3,5 triazine 2-yl)aminocarbonyl]benzene sulfonamide and mixtures thereof, 20 to 60% by weight of swelling bentonite, 5 to 15% by weight of anhydrous sodium sulfate, 10 to 25% by weight of urea, 2 to 10% by weight of polyethylene glycol having a weight-average molecular weight of from 200 to 600, 0–5% by weight of a die release agent selected from the group consisting of stearic acid, calcium stearate and magnesium stearate, 1 to 12% by weight of water and 0 to 30% by weight of an inert diluent.

2. The dry compactible herbicidal composition of claim 1 consisting of about 8 to 15% by weight of a herbicide selected from the group consisting of bromacil, diuron, bromacil-diuron complex, 3-cyclohexyl-6-(dimethylamino)-1-methyl-s-triazine-2,H(1H,3H)-dione, karbutilate, tebuthiuron, N-[(4,6-dimethoxy-1,3,-5-triazine 2-yl) aminocarbonyl]benzene sulfonamide and mixtures thereof, 30 to 50% by weight of swelling bentonite, 5 to 15% by weight of anhydrous sodium sulfate, 10 to 20% by weight of urea, 2 to 10% by weight of polyethylene glycol having a weight-coverage molecular weight of from 200 to 600, 1–4% of a die release agent selected from the group consisting of stearic acid, calcium stearate and magnesium stearate, 4 to 8% by weight of water and 10 to 25% by weight of an inert diluent.

3. The dry, compactible, water swellable herbicidal composition of claim 2 wherein the herbicide is 3-cyclohexyl-6-(dimethylamino)-1-methyl-s-triazine-2,H(1H,3H)-dione and the polyethylene glycol is polyethylene glycol 200.

4. A dry compacted, water swellable herbicidal pellet consisting essentially of the composition of claim 1, said pellet having a crushing strength greater than 3.7 kg/cm$^2$ and an impact resistance of at least 5.

5. A dry compacted, water swellable herbicidal pellet consisting essentially of the composition of claim 2, said pellet having a crushing strength greater than 3.7 kg/cm$^2$ and an impact resistance of at least 5.

* * * * *